United States Patent [19]

Petereit et al.

[11] Patent Number: 4,904,469

[45] Date of Patent: Feb. 27, 1990

[54] THERAPEUTIC AGENTS FOR ENZYMATIC WOUND CLEANING

[75] Inventors: Hans-Ulrich Petereit, Darmstadt; Gerhard Zeiss, Gross-Gerau, both of Fed. Rep. of Germany

[73] Assignee: Rohm GmbH Chemische Fabrik, Darmstadt, Fed. Rep. of Germany

[21] Appl. No.: 10,983

[22] Filed: Feb. 5, 1987

[30] Foreign Application Priority Data

Feb. 27, 1986 [DE] Fed. Rep. of Germany ....... 3606265

[51] Int. Cl.$^4$ .......................... A61K 37/54; A61K 9/70
[52] U.S. Cl. .................................... 424/94.3; 424/94.6; 424/94.62; 424/94.63; 424/94.1; 424/402; 424/443; 424/488
[58] Field of Search ................... 424/94.1, 94.21, 94.3, 424/94.6, 94.61, 94.62, 94.63, 94.64, 94.65, 94.66, 94.67, DIG. 13, 402, 404, 443, 446, 447, 488; 514/57; 435/179

[56] References Cited

U.S. PATENT DOCUMENTS

| | | |
|---|---|---|
| 2,973,300 | 2/1961 | Farrar Jr. et al. ................ 424/94.64 |
| 3,208,908 | 9/1965 | Maxwell et al. ..................... 424/94.6 |
| 3,627,876 | 12/1971 | Choay ................................ 424/94.6 |
| 4,405,324 | 9/1983 | Cruz Jr. ............................... 424/443 |

FOREIGN PATENT DOCUMENTS 682219 11/1952 United Kingdom ................ 424/446

Primary Examiner—Jacqueline M. Stone
Attorney, Agent, or Firm—Oblon, Spivak, McClelland, Maier & Neustadt

[57] ABSTRACT

The invention relates to a wound covering made from a polysaccharide base, particularly cellulose, which is formed as a fabric, which has a high absorbency due to its sponge-like structure and contains non-immobilized enzymes for wound therapy.

13 Claims, 1 Drawing Sheet

THERAPEUTIC AGENTS FOR ENZYMATIC WOUND CLEANING

BACKGROUND OF THE INVENTION

1. Field of the Invention

The invention relates to polysaccharide fabrics, such as cellulose, as host media for therapeutic, non-immobilizing enzymes, which are used as therapeutic agents for enzymatic wound cleansing.

2. Discussion of Background

The cleansing of wounds, which is a prerequisite for rapid healing, consists of the removal of necrotic tissue and pus. Enzymatic wound cleaning, in addition to surgical procedures and medical treatment with antiseptics or antibiotics, has proven valuable.

In the topical enzymatic therapy of wounds caused by injury, burns, skin diseases, etc., bandage materials having anything from relatively loose to tight fiber densities are used for the direct covering of the concerned portions of the body, including fabrics from fibrous materials that are natural and/or synthetic. High demands are therefore placed on their cleanliness, absorptive capacity and durability under the effects of secretions and medications.

According to statements in Deutsche Medizinische Wochenschrift, 85, 672 (1960), the local application of enzymes, such as with the enzyme preparation Jatrosin®, on compresses or gauze layers and the creation of a moist chamber by covering the same with a plastic film, achieved a more rapid healing of deep tissue necroses than with other known necrotic wound applications. Proteolytic enzymes, such as trypsin, chymotrypsin, papain, ficin, and bromelain as well as subtilisin, which is obtained from bacteria, are particularly well suited for the decomposition of necrotic tissue. Ribonucleases and deoxyribonucleases, such as streptodornase, are preferred to dissolve pus. Streptodornase in combination with streptokinase is also suitable for cleansing wounds of necrotic tissue and fibrin. The penetration of locally applied materials into the tissue can be promoted with the aid of the enzyme hyaluronidase.

The accelerated healing process achieved through therapy using such externally applied enzymes is based on the rapid decomposition of necrotic components and the promoted self-healing process which results. This comes as a result of the rapid filling of the tissue defect with granulation tissue, thus leading to an earlier formation of epithelial tissue.

The practical application of enzyme therapy consists of covering the wound with a section of a 4–6 layer gauze bandage prepared with enzymes. To achieve full effectiveness, it is necessary to create a moist chamber which can be sealed at the edges with zinc paste.

In DE-A 31 39 089 protein-based fabrics are proposed as enzyme carriers which can be used in procedures employing fabrics based on polysaccharides. This reference asserts that the use of collagen-based fabrics is particularly useful, since collagen has high water absorption and binding capabilities.

Despite these more favorable healing-promoting conditions, this form of application has not become widespread due to the very high price of collagen fabrics. The price ratio between collagen fabrics and common fabrics is about 1,000:1.

SUMMARY OF THE INVENTION

Accordingly, one object of the present invention is to provide a wound covering or bandage comprising enzymes, which promotes healing and does not interfere with the healing process of an organism.

A further object of the invention is to provide a wound covering or bandage using enzymes, which has a high water absorbency.

A further object of the invention is to provide a wound covering or bandage using enzymes which is inexpensive and easily prepared.

These objects and other objects of the invention which will become apparent from the following specification have been achieved by the wound covering for topical skin treatment of the present invention which comprises a sponge-like polysaccharide and at least one therapeutically effective enzyme in contact with said polysaccharide.

BRIEF DESCRIPTION OF THE DRAWING

The invention will become better understood by reference to the following specification when considered in conjunction with the accompanying drawing, wherein.

DETAILED DESCRIPTION OF THE PREFERRED EMBODIMENTS

Figure 1:
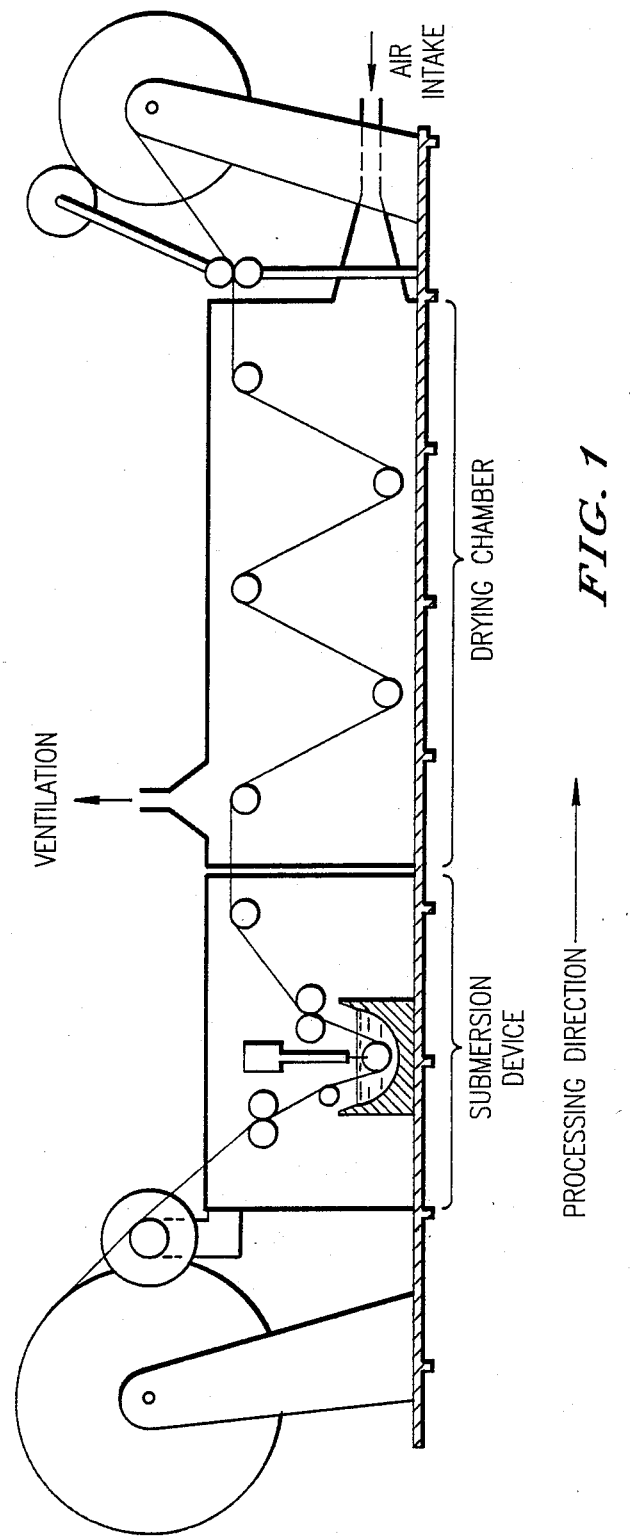
FIG. 1 shows a continuously operating immersion apparatus for the preparation of the wound covering of the present invention.

It has been discovered that the objectives stated above can be achieved to a large degree through the combined effects of known necrolyzing enzymes and a spongelike cellulose dressing or bandage used as an enzyme carrier and used to cover the wound. Because of its high absorption capability, this dressing provides for the rapid and continuous removal of liquid wound components.

The inventive wound covering is economical and accelerates wound cleansing and thereby more rapid and better healing of the wound. It also reduces practical difficulties, such as the problem of continuously supplying the enzyme to the wound, which is regulated in the present invention by the spongelike structure of the covering and the associated dissolving and diffusing processes, or by the frequent changing of the bandage. All of this results in noticeable simplifications in practice.

The novel bandage materials comprise textile fabrics which are known under the term "bonded fabrics" and have found broad practical use. All marketable fibers, i.e., natural such as plant fibers, as well as chemical fibers, are suitable for use in various manufacturing processes for these bonded fabrics. The fabrics that are particularly suitable for the enzyme-bandage material of the present invention are those fabrics comprised entirely or mostly of the economical fibrous raw materials based on polysaccharides, such as cellulose or spun rayon. Depending of the degree of prefabrication, the degree of porosity of these fabrics varies between 70 and 99%, particularly between 88 and 98%. The concept of degree of porosity is described in Roempps Chemie-Lexikon, 7th ed., p. 2784.

In comparison to the commonly used wound coverings based on collagen, the absorbency of the wound coverings according to the present invention is higher by a factor of from 1.5 to 5, and particularly 1.5 to 3.0.

The absorbency of the textile fabric to be used according to the invention is from 1500 to 3000% by weight of water, relative to the dry mass of the cellulose. It is determined by establishing the weight of a piece of fabric that has first been dried for 2 hours at 100° C., soaking it for 5 minutes in water at 20° C., and finally by dabbing away non-absorbed surface water and subsequent weighing. Accordingly, Absorbency (in % by weight water) =

$$\frac{\text{weight of fabric soaked in water}}{\text{weight of the fabric after drying at 100° C.}} \times 100$$

Suitable enzymes can be added to the polysaccharide carrier before or after the application. The above-mentioned enzymes, particularly proteases, are suitable, as are the appropriately used RN-ases and DN-ases and hyaluronidase. Proteolytic enzymes can also be employed in enzyme combinations. Of particular note is the pancreatic enzyme complex, which consists of trypsin, chymotrypsin, various peptidases and perhaps accompanying enzymes such as amylases and lipases. The individual enzymes can also be employed in novel combinations, particularly trypsin and chymotrypsin, and proteases of plant origin such as papain, bromelain and ficin, as well as proteases of microbiological origin, such as bacteria proteases, for example subtilisin. See Ullmans Encyklopaedie der Techn. Chemie, 4th edition, Vol. 10, p. 555, Verlag Chemie (1975).

The proteolytic activity of the individual enzymes is given in proteolytic units (PE). One proteolytic unit (PE) is the amount of enzyme which decomposes a 1.4% hemoglobin solution at pH 7.5 and 37° C. with an initial velocity such that the trichloroacetic acid soluble cleavage products formed in one minute at 280 nm have the same UV absorption as 10 microgram tyrosine. Preferred activity ranges are from about 10 to about 500 PE per $cm^2$ of the wound covering or bandage. Particularly preferred activity ranges are from 50 to about 250 PE per $cm^2$ of the wound covering or bandage.

The introduction of the enzymes to or into the porous, textile-like wound covering takes place, for example, with standardized enzyme solutions, such as in a physiological common salt solution, according to known methods, which meet standard hygienic and antiseptic requirements. In addition, in the placement and handling of the wound coverings with or without an enzyme application, purity and sterility must be strictly observed. These conditions can be achieved by a person skilled in the art using known means.

In addition to enzymes, the wound coverings according to the invention can contain other active ingredients, such as pharmaceuticals, antibiotics, hormones and their derivatives, salve components, and the like.

The fabric used for the wound coverings can be employed in layer thicknesses of 0.1 to 10 mm, preferably 1.5 to 2.5 mm, and in various length and width dimensions from, for example, 1 to about 100 cm. In some cases the covering will also require a moisture-sealing foil or film to form a moist chamber, whereby the side of the fabric opposite the skin carries the layer that is impervious to water.

The non-immobilized enzyme carrier material combinations according to the invention may find therapeutic application in several ways. Worth noting are illnesses in which portions of skin are attacked or destroyed. By way of example, the following are noted:

(a) burns, for example third degree burns;
(b) open ulcers (Dekubitus);
(c) ulcers on the lower extremities (Ulcus cruris);
(d) gangrene;
(e) acid burns;
(f) post-operative wound cleansing in skin transplantation; and
(g) traumatic skin wounds.

Having been described in general terms, the invention will now be further illustrated by the following examples which are presented to illustrate the invention only and are not intended to limit the scope of the invention which is defined by the appended claims.

EXAMPLES

Example 1

8.3 g of purified aseptic or low germ content trypsin is dissolved in a mixture of 9.4 g glycerin and 107.3 g of distilled water and is then sterile filtered through a membrane filter having 0.22 micron diameter pores.

Under aseptic conditions, 10 cellulose sponge pads, 2.5 mm thick 83×100 mm, are each uniformly moistened with 12.5 g of the enzyme solution.

After being dried for two days in a laminar flow device at room temperature, the preparations are coated on one side with a common self-adhering polyethylene film that is impervious to moisture and hermetically sealed in a package.

The enzymatic activity is on the average 180 PE per $cm^2$, which is almost 3 protease units per $cm^2$ according to the FIP. (Federation International Pharmaceutique (FIP) with headquarters in the Hague).

The resultant wound covering is flexible and can be fixed to the wound to be treated in a known manner. In this treatment, the wound covering is replaced after 24 hours.

Example 2

In a continuously operating immersion apparatus according to FIG. 1, a piece of bonded cellulose sponge fabric 20 m long and 10 cm wide (2.5 mm thick) is moistened by submersion in a sterile filtered enzyme solution having the following composition:

207.5 g of purified aseptic or low germ content trypsin, 235 g glycerin, 6.25 g Eudragit ® E 30D and 1282.5 g of purified water.

The pressure of the cylindrical rollers following the submersion step adjust the absorption of liquid in such a manner that 175 to 195 PE per $cm^2$, which is about 2.9 to 3.2 protease units per $cm^2$, according to FIP, are contained in the end product after passage through a drying tunnel (80°–90° C.).

The moisture proof covering is obtained by applying a commercial, self-adhering polyethylene film together with the sponge strips containing the protease to the spool at the end of the system.

Finally, under aseptic conditions, 10×10 cm pieces are cut and hermetically sealed.

Example 3

In a laminar flow device, each of 10 cellulose sponge pieces of 1 mm thickness (10×10 cm) are saturated with 15 g of a sterile filtered solution having the following composition:

900 mg of purified aseptic or low germ content trypsin, 2 mg of 5-nitro-2-furaldehyde semicarbozone (nitrofurazone), 5 g isopropanol, 1 g glycerin, 3 mg Eudragit ® E 30D and 9 g of water.

The moistened sponge pieces are dried and packaged in accordance with Example 1.

Obviously, numerous modifications and variations of the present invention are possible in light of the above teachings. It is therefore to be understood that within the scope of the appended claims, the invention may be practiced otherwise then as specifically described herein.

What is claimed as new and desired to be secured by Letters Patent of the United States is:

1. A wound covering for topical skin treatment, consisting essentially of
    (i) a sponge-like carrier consisting essentially of cellulose polysaccharide, and
    (ii) an enzymatically effective amount of at least one enzyme in contact with said polysaccharide, wherein said wound covering has an absorbency of 1,500 to 3,000% by weight of water, relative to the dry mass of said cellulose polysaccharide.

2. The wound covering of claim 1, wherein said enzyme is a member selected from the group consisting of proteases, ribonucleases, deoxyribonucleases, hyaluronidases and mixtures thereof.

3. The wound covering of claim 2, wherein said enzyme is a protease.

4. The wound covering of claim 2, wherein said enzyme is a ribonuclease or a deoxyribonuclease.

5. The wound covering of claim 1, further consisting essentially of therapeutic ingredients selected from the group consisting of pharmaceuticals and salves.

6. The wound covering of claim 5, wherein said therapeutic ingredient is a pharmaceutical selected from the group consisting of antibiotics, hormones and their derivatives.

7. The wound covering of claim 2, wherein said enzyme is a hyaluronidase.

8. The wound covering of claim 1, wherein said sponge-like polysaccharide is in a form comprising at least one layer.

9. The wound covering of claim 8, wherein said layer or layers are from about 0.1 to 10 mm thick.

10. The wound covering of claim 1, wherein said wound covering has an enzyme activity of between about 2.0 and 4.0 protease units per $cm^2$ (FIP).

11. The wound covering of claim 10, wherein said wound covering has an enzymatic activity between about 2.9 and 3.2 protease units per $cm^2$ (FIP).

12. The wound covering of claim 1, wherein said wound covering has a proteolytic activity between about 10–500 PE per $cm^2$.

13. The wound covering of claim 12, wherein said wound covering has a proteolytic activity between about 50–250 PE per $cm^2$.

* * * * *